United States Patent [19]
Miyoshi et al.

[11] Patent Number: 5,968,531
[45] Date of Patent: Oct. 19, 1999

[54] PARTICULATE COMPOSITE, METHOD OF PRODUCING THEREOF, AND COSMETIC CONTAINING PARTICULATE COMPOSITE

[75] Inventors: Taizo Miyoshi, Dayville; Shigeru Kishida, Storrs, both of Conn.

[73] Assignee: Miki America, Inc., Dayville, Conn.

[21] Appl. No.: 08/968,876

[22] Filed: Nov. 5, 1997

Related U.S. Application Data

[63] Continuation of application No. 08/796,450, Feb. 10, 1997, abandoned, which is a continuation of application No. 08/374,411, Dec. 30, 1994, abandoned.

[51] Int. Cl.⁶ ........................................................ A61K 7/48
[52] U.S. Cl. .............................................. 424/401; 424/69
[58] Field of Search ...................................... 424/401, 69

[56] References Cited

U.S. PATENT DOCUMENTS

| | | | |
|---|---|---|---|
| 3,656,982 | 4/1972 | Chapman et al. | 106/291 |
| 4,710,375 | 12/1987 | Takasuka et al. | 424/69 |
| 4,820,508 | 4/1989 | Wortzman | 106/297 |
| 4,863,800 | 9/1989 | Miyoshi et al. | 428/403 |
| 4,923,518 | 5/1990 | Brand et al. | 106/429 |
| 5,030,445 | 7/1991 | Hashimoto et al. | 424/59 |

FOREIGN PATENT DOCUMENTS

| | | |
|---|---|---|
| 1 231 831 | 1/1967 | Germany . |
| 3-181411 | 8/1991 | Japan . |

OTHER PUBLICATIONS

Database WPI/Derwent XP-002060182: Abstract for JP 5-017,327A (Jan. 26, 1993).

*Primary Examiner*—Jyothsna Venkat
*Attorney, Agent, or Firm*—Armstrong, Westerman, Hattori, McLeland & Naughton

[57] ABSTRACT

A particulate composite powder wherein each composite powder particle comprises a substrate particle surrounded by fine particles of metal oxide bound to the surface of the substrate particle by a binding agent containing at least one of metallic soap and wax, the amount of fine particles of metal oxide being between 10 and 30 wt % and the amount of said binding agent being between 0.5 and 5 wt % based on the total weight of substrate particles, fine particles of metal oxide and binding agent.

3 Claims, 2 Drawing Sheets

FIG. 1 X3000
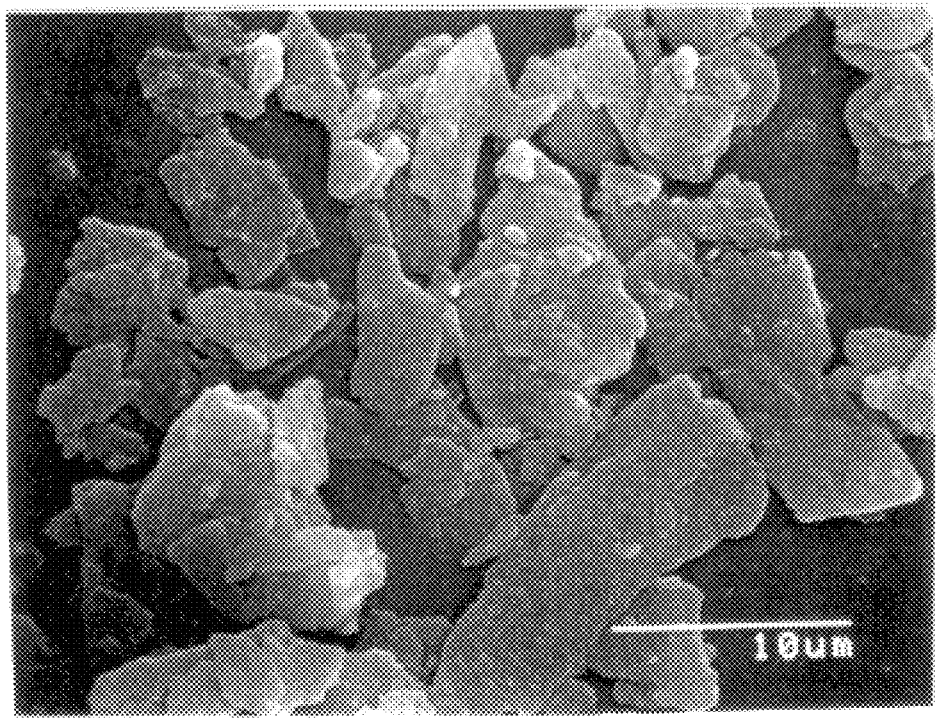
X15000
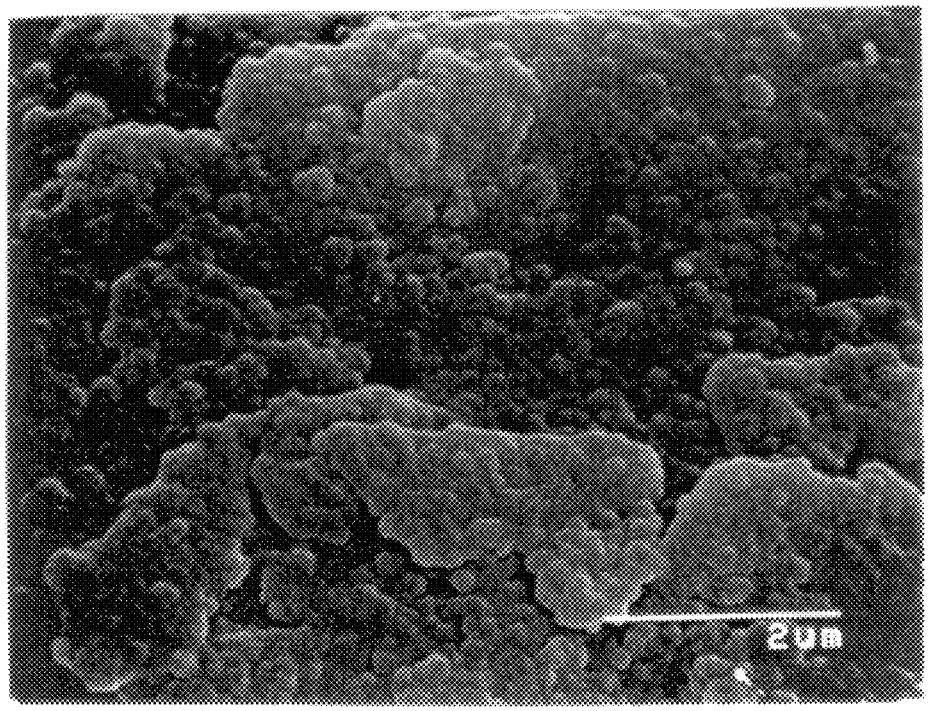
FIG. 2

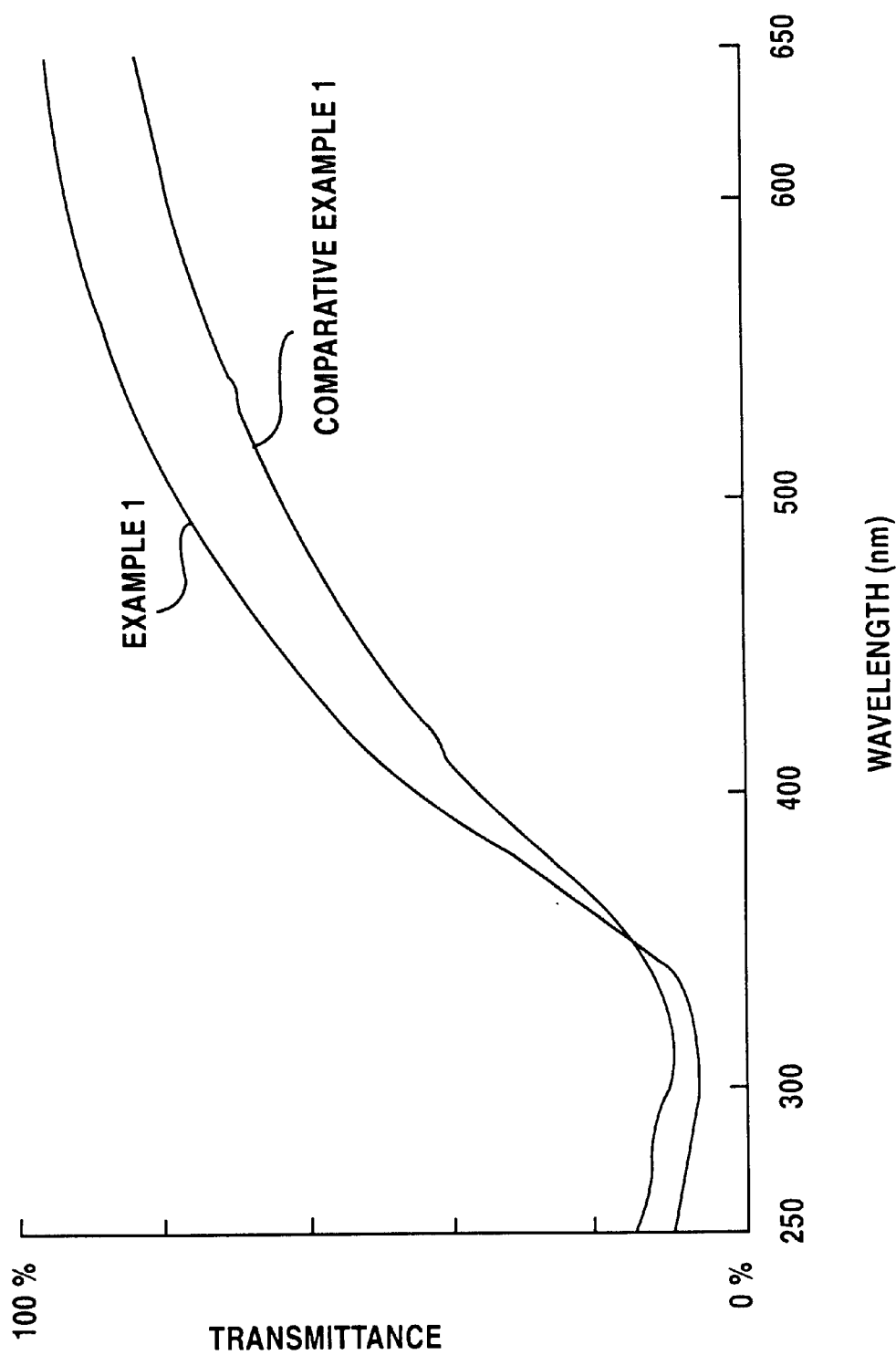

PARTICULATE COMPOSITE, METHOD OF PRODUCING THEREOF, AND COSMETIC CONTAINING PARTICULATE COMPOSITE

This application is a continuation of application Ser. No. 08/796,450 filed Feb. 10, 1997, now abandoned, which is a continuation of application Ser. No. 08/374,411 filed Dec. 30, 1994, now abandoned.

BACKGROUND OF THE INVENTION

This invention relates to a composite powder based on substrate particles coated with micronized metal oxides particles. The composite powder is particularly useful in cosmetics and skin care compositions. Most specifically, the invention relates to compressed powder cosmetics effective in protecting the skin against ultraviolet (UV) rays.

Known compressed powder foundations characterized by anti-ultraviolet protection incorporate in their formulations micronized titanium dioxide having a mean particle size of less than 100 nm. To achieve the desired protection from harmful ultraviolet rays, as much as 10% by weight or more of micronized titanium dioxide is used. The use of high amounts titanium dioxide having a mean particle size of less than 100 nm tends to result n agglomeration in the cosmetic, which in turn diminishes the protection against UV rays write also making the composition excessively opaque on the skin, a phenomenon known as "whitening effect". In addition, such compressed powder foundations have a scratchy and rough feel during and after application to the skin.

Another approach for imparting anti-UV protection to cosmetics is by incorporating liquid organic UV screeners such as octyl dimethyl PABA and ethylhexyl p-methoxy cinnamate. However, the use of such liquid UV screeners is limited to oil-based lotions and emulsion-type cosmetics. It is not possible to attain the desired protection from UV rays by using liquid organic UV screeners alone in compressed powder foundations.

Compressed powder foundations containing a composite of micronized titanium dioxide and thermoplastic bead-shaped powders are also known. A composite material is generally known as a complex material in which two or more individual substances are combined by physical and/or chemical means to form a single homogeneous material possessing structural and/or functional properties not present in any of the individual components. In the above-mentioned known composite of titanium dioxide and thermoplastic bead-shaped powders, as much as 30% by weight of the micronized titanium dioxide powder can be embedded on the surface of the thermoplastic powders. To attain the desired protection, a compressed powder foundation must contain up to 20% of this composite. The use of such relatively large amount of bead-shaped powder in compressed powder foundations not only presents problems with the compressibility of the composition, but also causes instability of the cosmetic in the container during transportation, particularly transportation by the cosmetic user. In addition, since the shape of the beads is spherical, the bead-shaped powders come off from the skin very easily and do not provide prolonged protection from UV rays when such protection is essential.

A method has been known for preparing and using titanium coated mica in published unexamined Japanese Patent Application (Application No. 5-87545). This method discloses mica only as a substrate and focuses on the relative transparency of the coated pigment as compared to conventional titanium coated mica or pearlescent pigment in general. In addition, this method uses titanyl sulfate as a starting chemical to form titanium dioxide, which means all the reaction must be carried out in an aqueous medium. This slurry process involves additional filtration, drying, and calcination at a temperature up to 900° C. to convert the hydrous oxide coating to crystalline oxide. Because of the high temperature of the calcination involved in this process, the base substrate is limited to materials capable of being stable at such high temperature. Moreover, the cost associated with the series of steps involved makes the use of the micronized titanium dioxide coated mica too expensive as a cosmetic substrate.

A method for preparing and using predispersed pigments on the flaky particulate by using a so-called "ordered mixture" mechanism is also known and is disclosed in a laid-open Japanese Patent Application (Application No. 5-214257). This method only concerns the dispersion mechanism of pigments having a particle size of less than 5 micron in substrates having an aspect ratio of 10 to 120. There is no indication in this method of the use of micronized titanium dioxide as a coating agent serving as a UV screener, and this method does not describe the use of a binder system.

U.S. Pat. No. 4,772,331 discloses a method for preparing colored flaky pigments comprising flaky substrates having a finely divided color pigment material adhered on the surfaces thereof by means of a high molecular weight organic binder. The patent limits the binder to high molecular weight organic compounds such a polyethylene glycols, polypropylene glycols or polyvinyl pyrrolidones having a molecular weight of from about 500 to 160,000. Since all the reaction must take place in the liquid medium, this method presents not only the potential problem of agglomeration of the colored pigments during the drying process, but also the problem that the cost associated with the filtration, drying, and pulverizing steps makes the material produced from this process too expensive for use as a cosmetic substrate.

BRIEF SUMMARY OF THE INVENTION

One object of the invention is to provide a composite powder comprised of composite particles, each composite particle comprising a substrate particle coated with particles of micronized metal oxide particles securely bound to the substrate particle by a binding agent containing at least one member selected from the group consisting of metallic soap and wax.

Another object of the invention is to provide a method for preparing the above-described composite powder.

Yet another object of the invention is to provide a cosmetic composition containing the above-described composite powder which has a smooth, lubricious and pleasant feel on the skin and retains its transparency.

BRIEF DESCRIPTION OF THE DRAWINGS

FIG. 1 and FIG.2 are photographs of the particulate composite according to the present invention.

FIG.3 shows the UV/Visible range spectrometer transmittance test conducted in Example 1 and Comparative Example 1 described hereinafter.

DETAILED DESCRIPTION OF THE PREFERRED EMBODIMENTS

The composite powder of the invention consists essentially of composite particles, wherein each composite particle is composed of a substrate particle (or core particle) which is coated with a plurality of fine particles of metal oxide. The fine particles are spread over the surfaces of the substrate particle and are bound to those surfaces with a binding agent containing at least one member selected from the group consisting of metallic soap and wax.

The substrate or core particles may be organic powders or inorganic powders of various shapes. However, for use in pressed powder cosmetics, substrate particles having non-spherical shapes are preferred, such as lamellar particles or particles in the shapes of leaves, flakes or platelets. Examples of such non-spherical substrate particles include, but are not limited to, talc, mica, sericite, kaolin and synthetic fluorphlogopite mica used singly or in combination. For most cosmetic formulations, substrate particles having an average particle size in the range of 1–20 micron (measured by laser diffraction on volume basis) are suitable. Alternatively, substrate particles having a diameter in the range of 1–50 micron and an aspect ratio of at least 10 are suitable for most cosmetic formulations.

The fine particles of metal oxides are metal oxide particles having a mean particle size which is at most one-tenth of the mean particle size of the substrate particles. For use as UV screeners in cosmetic compositions, micronized particles of metal oxides must have an average particle size (measured by laser diffraction on volume basis or by SEM observation) of less than 100 nm to be effective in minimizing the penetration of UV rays which have a wavelength from 200 to 400 nm. The micronized metal oxide particles optionally may be coated with alumina or silica to reduce the relatively high photochemical reactivity of micronized metal oxide. For cosmetic formulations, micronized titanium dioxide and micronized zinc oxide, used singly or in combination, are particularly suitable as UV screeners.

The fine particles of metal oxides are bound to the substrate particles by a binding agent (containing at least one member selected from the group consisting of metallic soap and wax) which also facilitates dispersion of the metal oxide particles over the surfaces of the substrate particles before those metal oxide particles become bound to the substrate particles. Examples of metallic soaps suitable for cosmetics include, but are not limited to, the aluminum, calcium, lithium, magnesium, titanium, zinc and zirconium salts of cosmetically acceptable fatty acids. The metallic soaps and wax may be used singly or in combination. The metallic soap or wax is a solid which can be softened and partially melted at a temperature of less than 220° C., preferably less than 160° C., with the melting point being no less than 60° C. A metallic soap or wax with a melting point higher than 160° C. will need a much longer processing time before the metallic soap or wax is softened or partially melted to form a film around the substrate, and such longer processing time tends to cause agglomeration of the fine particles metal oxide during the process. With a melting point of less than 60° C., the composite obtained by using such low melting metallic soap or wax is not stable enough and presents potential problems such as segregation and agglomeration of the fine particles of metal oxide in the cosmetic formulation in the long term. Moreover, the metallic soap or wax with a melting point of less than 60° C. tends to have a tacky feel and thus it is not desirable for use in cosmetic formulations.

In conjunction with a metallic soap or wax, additional chemicals can be optionally used as surface treating agents to impart the desired characteristics to the composite powder once the composite powder is obtained. Examples of such surface treating agents include, but are not limited to, hydrogenated lecithin, amino acids and low molecular weight dimethylpolysiloxane. Those surface treatment processes can be carried out by separate methods as described in U.S. Pat. No. 4,606914 and U.S. Pat. No. 4,622,074 after the composite powder is obtained. Each of these additional treating agents imparts desired physical attributes such a desired aesthetic feel, pressability, or improved transparency on the skin.

The weight proportion of fine particles of metal oxide to substrate particles depends on the desired degree of coating of the substrate particles as well as the relative sizes of the two types of particles. In general, however, between 10 and 30 wt % of the fine particles of metal oxide should be used (based on the total weight of substrate particles, fine particles of metal oxide, and binding agent containing at least one member selected from the group consisting of metallic soap and wax) to attain acceptable UV screening effect and avoid segregation and agglomeration of the fine particles of metal oxide. For cosmetic formulations, the amount of fine particles of metal oxide is preferably in the range of 20–25 wt % based on the total weight of substrate particles, fine particles of metal oxide, and binding agent containing at least one member selected from the group consisting of metallic soap and wax.

The amount of binding agent containing at least one member selected from the group consisting of metallic soap and wax in the composite powder is usually in the range between 0.5 and 5 wt % based on the total weight of substrate particles, fine particles of metal oxide and binding agent containing at least one member selected from the group consisting of metallic soap and wax. The optimum amount of binding agent depends on the ratio of substrate particles to fine particles of metal oxide, and on their relative surface areas. In cosmetic formulations, the use of more than 5wt % of the binding agent causes deterioration in the UV screening effect of the fine particles of metal oxides, and also reduces the transparency of the composition on the skin. On the other hand, an amount of binding agent which is less than 0.5wt % is insufficient to have the fine particles of metal oxide bound to the substrates securely for consistent UV screening effect, and, moreover, such composition leads to instability of the composite powder such as agglomeration of the fine particles of metal oxides by themselves or segregation of the fines particles of metal oxide from the substrates.

The composite powder is prepared by bringing the substrate particles in contact with the fine particles of metal oxide in the presence of the binding agent (containing at least one member selected from the group consisting of metallic soap and wax) at a temperature where the binding agent is softened and at least partially melted, and blending rapidly the resulting mixture. To bring up the temperature during the mixing process, it is preferred to use the heat generated from the friction of the blades to the mixer container during a prolonged process time and/or the heat supplied by using an equipped jacket. A high rpm mixer provided with heating capacity may be used for preparing the composite powder. In a batch type mixer, the tip speed of the blades is preferably above 40 m/sec to obtain satisfactory powder collision frequency, and the total volume of the components prior to mixing should be in the range of 30–60% of the mixer capacity of the batch type mixer. The combined action of heating and blending results in the formation of a film of the binding agent on the surface of the substrate particles. This film serves to bind the fine particles of metal oxide to the surface of the substrate particle.

It is essential not to use any liquid medium or solvent such as water in the process of the present invention. Not only does such liquid medium cause agglomeration of the fine particles of metal oxide during the process, but the liquid medium also causes agglomeration of the composite powder itself, resulting in difficulties in usage during the cosmetic formulation. The method of the present invention offers many advantages over the prior art methods utilizing a solvent system. Since the method of the invention can be carried out in a closed batch-type mixer where the only processing medium is gaseous, the fine particles of metal oxide tend to be free of agglomerates. Other than ordinary air, other various gases can be used. Nitrogen or argon gases are specifically beneficial for some processes involving rather unstable materials such as metallic soaps containing unsaturated fatty acids. The ratios of the components are more accurately reflected in the actual composite powder product, in contrast to the ratios obtained with prior art methods such as the slurry process in which some of the components including the coating agent such as titanyl sulfate can be potentially washed away with the liquid medium at the time of filtration. Moreover, the method of the invention does not involve any further process such as filtration, calcination, drying, and pulverizing as is often required in the prior art methods.

The present invention is further illustrated in the following Examples to which the invention is not in any way limited. In all the Examples and Comparative Examples described below, the capacity of the mixer was 5 liters.

EXAMPLE 1

Mixture of 200 g of talc with mean particle size on volume basis by laser diffraction of 8.2 micron (Soft talc from Miki America, Inc.) and 67 g of micronized titanium dioxide with mean particle size on volume basis by laser diffraction of 0.042 micron (UFTR from U.S. Cosmetics Co.) was mixed with 5.3 g of USP grade zinc stearate wit meting point of between 115° C. and 125° C. (Witco Co.) in Mizuho MP-5 mixer for 30 minutes. The tip speed of the blades was set at 40 m/sec and the temperature of the powders inside of the mixer at the end of the process was 120° C., The sample had low oil absorption, good sheerness and slip, and uniform attachment of the micronized titanium dioxide on the surface of the talc was confirmed by SEM observation. FIG. 1 and FIG. 2 are the SEM photographs of the composite powder obtained in Example 1. To test the stability of the composite, the composite sample was stirred in the water in the beaker to see if micronized titanium dioxide can be detached. However, water was clear after 50 stirs by spoon, and the composite sample showed no disintegration in water. Additional test for the stability of the sample was carried out. The mixture of 0.5 grams of the sample in 20 ml of ethyl alcohol in a test tube was put in the ultrasonic cleaner (Branson 1200) for five minutes. After four hour the clarity of the ethyl alcohol was observed for the detachment due to the ultrasonic energy and subsequent suspension of the fine particles of metal oxide in ethyl alcohol. The solution was clear after four hours and therefore the result confirmed the attachment of the fine particles of titanium dioxide over the talc. The sample was further tested for its UV transmittance by UV/visible range spectrometer (Shimadzu UV 160) for its UV screening effect. FIG. 3 shows UV/visible range spectrometer test result, and it has very low transmittance in the UV-A and B range while maintaining high transmittance over the visible ranges.

COMPARATIVE EXAMPLE 1

Mixture of 200 g of talc with mean particle size on volume basis by laser diffraction of 8.2 micron (Soft talc from Miki America, Inc.) and 67 g of micronized titanium dioxide with man particle size on volume basis by laser diffraction of 0.042 micron (UFTR from U.S. Cosmetics Co.) was mixed with 5.3 g of USP grade zinc stearate with melting point of between 115° C. and 125° C. (Witco Co.) in Mizuho MP-5 mixer for 30 minutes. The tip speed of the blades was set at 30 m/sec and the temperature of the powders inside of the mixer at the end of the process was 80° C.

The sample had very high oil absorption, unsatisfactory sheerness and rough feel, The sample was tested for stability in water, and micronized titanium dioxide detached in water as soon as the sample was introduced in the water. In addition, ultrasonic test described in Example 1 showed the detachment of micronized titanium dioxide from the talc. FIG. 3 shows UV/visible range spectrometer test result, and it has higher transmittance in the UV-A and B range while maintaining unsatisfactory transmittance over the visible ranges compared with the test result obtained from Example 1.

EXAMPLE 2

Mixture of 200 g of mica with mean particle size on volume basis by laser diffraction of 5.8 micron (mica MRP from Rona) and 67 g of micronized zinc oxide (UFZO from U.S. Cosmetics Co.)with mean particle size of less than 0.02 micron by SEM observation was mixed with mixture of 5.3 g of USP grate magnesium stearate with melting point of between 110° C. to 135° C. (Witco Co.) and 2.0 g of hydrogenated egg oil (HEON from Miyoshi Kasei, Inc., Japan) in Mizuho MP-5 mixer for 30 minutes.

Tip speed of the blades was set at 40 m/sec and the temperature of the powders inside of the mixer at the end of the process was 120° C.

The sample had low oil absorption, good sheerness and slip, and uniform attachment of micronized zinc oxide is confirmed by SEM observation. The sample was tested for the stability in water as described in Example 1, and the water was clear after 50 stirs.

The ultrasonic t described in Example 1 was also repeated, and the test confirmed that the composite obtained had no detachment of micronized zinc oxide.

COMPARATIVE EXAMPLE 2

Mixture of 170 g of mica with mean particle size on volume basis by laser diffraction of 5.8 micron (mica MRP from Rona) and 95 g of micronized zinc oxide (UFZO from U.S. Cosmetics Co.) with mean particle size of less than 0.02 micron by SEM observation was mixed with 8.0 g of USP grade zinc stearate with melting point of between 110° C. and 135° C. (Witco Co.) in Mizuho MP-5 mixer for 30 minutes.

The tip speed of the blades was set at 40 m/sec and the temperature inside of the mixer at the end of the process was 120° C.

The sample had high oil absorption and unsatisfactory sheerness or slip. In addition, micronized zinc oxide was detached in water during the stability test depicted in Example 1.

In addition, Ultrasonic test described in Example 1 showed the detachment of micronized zinc oxide from the mica.

COMPARATIVE EXAMPLE 3

Mixture of 200 g of mica with mean particle size on volume basis by laser diffraction of 5.8 micron (mica MRP from Rona) and 67 g of micronized zinc oxide (UFZO from U.S. Cosmetics Co.) with mean particle size of less than 0.02 micron by SEM observation was mixed with 15.0 g of USP grade zinc stearate with melting point of between 110° C. and 135° C. (Witco Co.) in Mizuho MP-5 mixer for 30 minutes.

The tip speed of the blades was set at 40 m/sec and the temperature inside of the mixer at the end of the process was 120° C.

The sample had low oil absorption but has very rough feel on the skin. Moreover, the sample had excessive skin adhesion and therefore excessive opacity on the skin. However, micronized zinc oxide was stable in water during the ability test depicted in Example 1.

In addition, Ultrasonic test described in Example 1 showed the attachment of micronized zinc oxide from the mica. However, UV transmittance test revealed the unacceptably low UV screening effect as well as very low transmittance over the visible ranges.

COMPARATIVE EXAMPLE 4

Mixture of 200 g of mica with mean particle size on volume basis by laser diffraction of 5.8 micron (mica MRP from Rona) and 67 g of micronized zinc oxide (UFZO from U.S. Cosmetics Co.) with mean particle size of less than 0.02 micron by SEM observation was mixed in Mizuho MP-5 mixer for 30 minutes.

The tip speed of the blades was set at 40 m/sec and the temperature inside of the mixer at the end of the process was 120° C.

The sample had high oil absorption and unsatisfactory sheerness or slip. In addition, micronized zinc oxide was detached in water during the stability test depicted in Example 1.

Moreover, Ultrasonic test described in Example 1 showed the detachment of micronized zinc oxide from the mica.

COMPARATIVE EXAMPLE 5

Mixture of 200 g of talc with mean particle size on volume basis by laser diffraction of 8.2 micron (Soft talc from Miki America, Inc.) and 67 g of micronized titanium dioxide with mean particle size on volume basis by laser diffraction of 0.042 micron (UFTR from U.S. Cosmetics Co.) was mixed with 1.2 g of USP grade zinc stearate with melting point of between 115° C. and 125° C. (Witco Co.) in Mizuho MP-5 mixer for 30 minutes. The tip speed of the blades was set at 40 m/sec and the temperature of the powders inside of the mixer at the end of the process was 120° C.

The sample had high oil abosrption and unsatisfactory sheerness or slip. In addition, micronized titanium dioxide was detached in water during the stability test depicted in Example 1. Moreover, Ultrasonic test described in Example 1 showed the detachment of micronized titanium dioxide from the talc,

COMPARATIVE EXAMPLE 6

Mixture of 200 g of mica with mean particle size on volume basis by laser diffraction of 5.8 micron (mica MRP from Rona) and 67 g of micronized zinc ode (UFZO from U.S. Cosmetics Co.) with mean particle size of less than 0.02 micron by SEM observation is mixed with 5.3 g of polyethylene glycol 600 with average molecular weight of about 550 g per mole in Mizuho MP-5 mixer for 30 minutes. The tip speed of the blades was set at 40 m/sec and the temperature of the powders inside of the mixer at the end of the process was 120° C.

The material obtained had high oil absorption and unsatisfactory sheerness or slip. In addition, micronized zinc oxide was detached in water during the stability test depicted in Example 1.

EXAMPLE 3

The compressed powder foundation is prepared by using the sample obtained in Example 1.

| | |
|---|---|
| Sample from Example 1 | 35.0 wt % |
| Metal soap treated sericita | 28.0 wt % |
| Hydrogenated lecithin treated mica | 7.0 wt % |
| Dimethicone treated titanium dioxide | 10.0 wt % |
| Dimethicone treated yellow iron oxide | 2.5 wt % |
| Dimethicone treated red iron oxide | 0.8 wt % |
| Dimethicone treated black iron oxide | 0.3 wt % |
| Silica beads SB-700 | 4.0 wt % |
| 2-Octyldodecyl Oleate | 4.0 wt % |
| Dimethicone oil, 20 cst | 8.2 wt % |
| Preservatives | 0.2 wt % |

The obtained compressed powder foundation had a pleasant and smooth feel on the skin and exhibited no "whiteness" in spite of the high content of titanium oxide.

The particular embodiments of the invention in which metallic soap is used as a binding agent and the substrate particles are non-spherical possess the following additional advantages. The metallic soap functions not only to bind the fine particles of metal oxide to the substrate particles, but the metallic soap also imparts properties which are extremely desirable in powder-based cosmetics, namely lubricious feel and long wear. The use of non-spherical particles also enhances the appearance and wear of the powder-based cosmetics.

The use of metallic soap as a binding agent also results in a powder composite which is hydrophobic so that it is suitable for dual foundations and provides prolonged protection against UV rays under outdoor conditions.

The composite powder of the invention is characterized by strong and lasting binding of the fine particles of metal oxide to the substrate particles. There is very little separation of the fine particles of metal oxides from the substrate particles, even after the composite powder has been subjected to mixing and stirring in a liquid, slurry or powder medium and after being applied to the skin in the form of a cosmetic. Therefore, when the composite powder is used as a UV screener in a cosmetic formulation, long-lasting protection is achieved.

In cosmetic applications, the composite powder of the invention may be used to formulate not only pressed powder cosmetics, but also other forms of cosmetics such as non-pressed powder cosmetics, lipsticks, creams, lotions and aerosol sprays.

We claim:

1. A cosmetic composition comprising a particulate composite which comprises composite particles, each of said particles comprising a substrate particle surrounded by a plurality of fine particles of metal oxide bound to the surface of the substrate particle by a binding agent containing at least member selected from the group consisting of metallic soap and wax, wherein said plurality of fine particles has a mean particle size of less than 100 nm, the amount of said fine particles of metal oxide is between 10 and 30 wt. % and the amount of said binding agent is between 0.5 and 5 wt. % based on the total weight of said substrate particles, said fine particles of metal oxide and said binding agent, and wherein said particulate composite is prepared by a process comprising the steps of bringing said substrate particles in contact with fine particles of metal oxide in the presence of said binding agent at a temperature where the binding agent is softened and at least partially melted, and blending the resulting mixture without any aid of a liquid medium or solvent as a processing agent, wherein said particles of fine metal oxide are particles of at least one member selected from the group consisting of micronized titanium dioxide and zinc oxide; and wherein said substrate particle is at least one member selected from the group consisting of talc, mica, sericite, kaolin and synthetic fluorphlogopite mica.

2. A cosmetic composition as in claim 1, wherein said metallic soap is at least one selected from the group consisting of aluminum, calcium, lithium, magnesium, titanium, zinc and zirconium salts of cosmetically acceptable fatty acids.

3. A cosmetic composition as in claim 1, wherein said wax is at least one hydrogenated triglyceride.

* * * * *